United States Patent
Moine et al.

(10) Patent No.: US 11,331,407 B2
(45) Date of Patent: May 17, 2022

(54) SKIN-ADHESIVE ITEM

(71) Applicant: ELKEM SILICONES FRANCE SAS, Lyons (FR)

(72) Inventors: Caroline Moine, Sorbiers (FR); Gaelle Cros, Ternay (FR)

(73) Assignee: ELKEM SILICONES FRANCE SAS, Lyons (FR)

( * ) Notice: Subject to any disclaimer, the term of this patent is extended or adjusted under 35 U.S.C. 154(b) by 0 days.

(21) Appl. No.: 16/629,302

(22) PCT Filed: Jul. 2, 2018

(86) PCT No.: PCT/FR2018/000187
§ 371 (c)(1),
(2) Date: Jan. 7, 2020

(87) PCT Pub. No.: WO2019/008238
PCT Pub. Date: Jan. 10, 2019

(65) Prior Publication Data
US 2020/0222578 A1 Jul. 16, 2020

(30) Foreign Application Priority Data
Jul. 7, 2017 (FR) .................................... 1700725

(51) Int. Cl.
| | | |
|---|---|---|
| A61L 15/58 | (2006.01) | |
| C09J 7/38 | (2018.01) | |
| C08G 77/12 | (2006.01) | |
| C08G 77/16 | (2006.01) | |
| C09J 183/04 | (2006.01) | |
| C08G 77/00 | (2006.01) | |

(52) U.S. Cl.
CPC .............. *A61L 15/58* (2013.01); *C08G 77/12* (2013.01); *C08G 77/16* (2013.01); *C08G 77/70* (2013.01); *C09J 7/38* (2018.01); *C09J 183/04* (2013.01)

(58) Field of Classification Search
CPC ......... C08L 83/00; C08L 83/04; C09J 183/04; C09J 2401/006; C09J 2423/106; C09J 2427/006; C09J 2467/006; C09J 2475/006; C09J 2483/00; C09J 7/38; A61L 24/046; A61L 15/58; C08K 5/56; C08G 77/12; C08G 77/16; C08G 77/20; C08G 77/70

See application file for complete search history.

(56) References Cited

U.S. PATENT DOCUMENTS

| | | |
|---|---|---|
| 3,159,601 A | 12/1964 | Ashby |
| 3,159,602 A | 12/1964 | Hamilton et al. |
| 3,220,972 A | 11/1965 | Lamoreaux |
| 3,419,593 A | 12/1968 | Willing |
| 3,508,947 A | 4/1970 | Hughes |
| 3,775,452 A | 11/1973 | Karstedt |
| 2011/0212325 A1* | 9/2011 | Determan ............... A61L 15/58 428/332 |
| 2015/0203618 A1 | 7/2015 | Allen et al. |

FOREIGN PATENT DOCUMENTS

| | | |
|---|---|---|
| EP | 0057459 | 8/1982 |
| EP | 0188978 | 7/1986 |
| EP | 0190530 | 8/1986 |
| EP | 0537086 | 4/1993 |

OTHER PUBLICATIONS

International Search Report and Written Opinion dated Sep. 27, 2018 in corresponding International Patent Application No. PCT/FR2018/000187, filed Jul. 2, 2018, 12 pages.

Bluestarsilicones, "Silcolease PA PSA 502 Technical Data Sheet", (Oct. 1, 2016), URL: https://silicones.elkem.com/EN/our_offer/Product/90060535/_/SILCOLEASE-PSA-502, (Mar. 8, 2018), 2 pages.

* cited by examiner

*Primary Examiner* — Frances Tischler
(74) *Attorney, Agent, or Firm* — Sheppard, Mullin, Richter & Hampton LLP

(57) ABSTRACT

A skin-adhesive item is described that can include a substrate F coated continuously or discontinuously on at least one of the two faces thereof by a pressure-sensitive silicone adhesive Z that has been previously sterilized by means of gamma radiation and demonstrates good tack on the skin even after sterilization.

15 Claims, No Drawings

SKIN-ADHESIVE ITEM

CROSS-REFERENCE TO PRIOR APPLICATIONS

This application is a National Stage of PCT/FR2018/000187, filed Jul. 2, 2018, and designating the United States (published on Jan. 10, 2019, as WO 2019/008238A1) which claims priority under 35 U.S.C. § 119 to French Patent Application No. FR 1700725, filed Jul. 7, 2017, each hereby expressly incorporated by reference in its entirety and each assigned to the assignee hereof.

The present invention relates to a skin-adhesive article comprising a substrate F, coated continuously or noncontinuously, on at least one of the two faces with a pressure-sensitive silicone adhesive Z which has been sterilized by means of gamma radiation and which exhibits a good tack on the skin, even after sterilization.

The global market for wearable medical devices is rapidly expanding. This very strong growth is explained in particular by the runaway integration of wireless communication technologies which are opening numerous perspectives for the long-range monitoring of patients and improvement in care benefits. With this growth in long-range monitoring and the change to ambulatory and home care, more and more patients are wearing medical devices fixed to the skin. In addition to sensors for monitoring the heart rate, ostomy appliances, wearable medical devices include novel advanced functionalities, such as, for example, the monitoring of skin exposure to ultraviolet (UV) rays, the blood glucose level, and the like. This diversity of devices, the operation of which requires an adhesion to the skin, comes along with the use of dressings having medical or paramedical use. The majority of adhesives currently used to attach, to the skin, wearable medical devices or dressings for the care of wounds have the disadvantage of adhering very strongly to the skin. The sensory perception experienced during the detachment from the skin of such adhesives after only a few hours of use is generally rather unpleasant and can even cause damage to the epidermal layer of the skin.

Adhesives in the form of a gel based on polyurethane or on silicone provide an alternative to pressure-sensitive adhesives and are less painful for the patient on use. However, polyurethane-based gels have problems of cytotoxicity which limit their use for a skin-contact usage. As regards silicone gels, the ionizing radiation used for the sterilization of some medical devices has a particularly detrimental effect, in particular on their properties of adhesion to the skin (or tack). It is for this reason that adhesives made of silicone gel are sterilized using a technique of sterilization by ethylene oxide which remains problematic in its implementation insofar as this gas is toxic. Furthermore, this sterilization process is expensive and has unfavorable impact on the manufacturing costs of any wearable medical devices using this type of adhesive.

In the case of a medical device, a sterilization is generally defined by theoretical probability of the presence of viable microorganism on this same device of less than or equal to 1 per $10^6$ colony-forming unit (CFU/ml). Several reference standards have been established in order to set up a system for the strict control of the sterilization of these devices. Examples of sterilization technique are:
  sterilization by ultraviolet (UV) radiation: this sterilization method is more employed in research as a result of its low operating cost. However, its main disadvantage is that this method is not fungicidal, that is to say that it does not make it possible to kill all the microorganisms;
  sterilization by autoclave: this sterilization method is widely used in hospitals for the sterilization of surgical instruments, textiles, dressings, glassware, rubber and some plastics. This is a reference process for sterilization due in particular to its ease of use, to its low cost and to its nontoxicity to the environment. The principle is based on the use of pressurized saturated steam as sterilizing agent which, under the effect of the heat and the moisture, makes possible destruction of the contaminants by coagulation and denaturation of proteins by hydrolysis. However, the effectiveness of this sterilization depends on the operating parameters, which are the duration of the cycle, the temperature, the pressure and the degree of humidity. Furthermore, this sterilization technique is not suitable for heat-sensitive or water-sensitive materials and can only be applied to polymers which are resistant to high temperatures;
  sterilization by chemical treatment, in particular:
    sterilization by exposure of the medical device to ethylene oxide: ethylene oxide is a cyclic ether which is a gas at atmospheric pressure and at ambient temperature. The sterilizing action of this compound is due to its reactivity with regard to the amino groups of the nucleic acids of the microorganisms. The disadvantage of this process is that ethylene oxide is a gas which is toxic to man (carcinogenic and mutagenic). Furthermore, this process requires removing the toxic residues which are the derivatives of ethylene oxide, such as ethylene chloride and ethylene glycol; and
    sterilization by plasma: cold plasmas are brought about by subjecting a gas (or a gas mixture) to an electric field while operating either at atmospheric pressure or at reduced pressures of the order of $10^-$ millibars which will generate UV radiation and reactive oxygen entities which remove the pathogenic agents; and
  sterilization by ionization: this technique is more particularly intended for heat-sensitive materials. This sterilization method is widely employed on the industrial scale and comprises two alternative forms: beta sterilization and gamma sterilization:
    sterilization by beta (β) irradiation is generally employed in the laboratory to sterilize certain materials; however, due to the high degradation of the materials, it is not used to any great extent in the sterilization of medical devices, and
    sterilization by gamma (γ) rays is widely used in the medical field. Radiation (doses of between 15 and 50 kGy) is emitted by synthetic cobalt-60 which results in the destruction of the DNA and the RNA of the pathogenic agents, preventing their replication and expression of the genes. This method exhibits a major disadvantage related to the fact that some materials can be damaged by this gamma radiation.

For medical devices, as soon as the aspect of the contact with the skin is required, the sterility of the material in contact with the skin is a major safety criterion for a large number of medical devices and cannot be omitted as its absence can have serious consequences. Nevertheless, although gamma sterilization is very widely used in the medical field, this technique exhibits a major challenge for adhesives as, after treatment, they still have to make it possible to keep the medical devices firmly in contact with the skin while avoiding the discomfort brought about during the detaching of such adhesives from the skin. Control of the post sterilization adhesion properties thus remains key as it is desired for them to be remain stable even after this treatment, all the more so since the gamma treatment doses used in the medical industry vary from 15 to 50 kGy, which makes the control and the maintenance of the performance of adhesive even more problematic.

Mention may be made, among the adhesives which are commonly used in wearable medical devices and which are in contact with the skin, of silicone-based pressure-sensitive adhesives (PSAs) which are capable of adhering to a surface simply by contact or under the effect of a light pressure. They exhibit major advantages with respect to acrylic adhesives. This is because not only can acrylic adhesives bring about irritation of the skin in some patients but also have a tendency to increase the adhesion of the skin with the passage of time, making it problematic to reposition the medical device. PSAs made of silicone are ideally suited to the enhanced requirements of novel wearable medical devices as a result of their biocompatibility and of their permeability, making possible the diffusion of oxygen, carbon dioxide and water vapor, which renders them perfectly suited to medical applications in which enhanced aeration is necessary. However, the adhesion to the skin has to be maintained in a comfort zone for the patient in order to prevent this sensory discomfort related to the phases of detachment of the medical device.

The term "pressure-sensitive adhesives" (PSAs), as used in the present statement, relates to adhesives which can adhere to a surface and be detached therefrom without there being transfer of significant amounts of adhesive onto the surface and which can be again adhesively bonded to the same or to another surface as the adhesive retains a portion or all of its tackiness and of its adhesive force.

Pressure-sensitive silicone adhesive compositions are evaluated in terms of properties of adhesion to the skin or "tack" and of peel strength. The tack characterizes the adhesiveness of a pressure-sensitive adhesive and brings two factors into play: the nature of the bonds which are instantaneously created with the support and the viscoelasticity of the adhesive.

In order to assess and evaluate the tack, a "Probe Tack" method is known and is described in the standard ASTM D2979. This test makes it possible to measure the instantaneous adhesion of the adhesive. The principle is as follows for the silicone PSA adhesives described in the present statement: a cylindrical flat-faced punch is brought into contact with the adhesive film which is deposited on the substrate. The punch is subsequently kept in contact with a silicone PSA for a contact time of one second at a constant pressure of 100 gf/cm$^2$. Subsequently, the punch is detached at a constant rate of 10 mm/s from the gel, and the force necessary to separate the adhesive from the rod is measured and is expressed in gf/cm$^2$ while the detachment energy for its part is expressed in mJ/cm$^2$. In the present statement, when reference is made to the tack property at the skin, this property is evaluated via the detachment energy of the PSA tested.

The adhesiveness or peel strength of a silicone adhesive on the skin is the force necessary to detach it from a sheet of Bristol paper, which simulates the skin, of well defined size, at an angle of 180° and at a constant rate of 300 mm/min and with the help of a 10N (Newtons) force cell in the case of silicone gels. It is evaluated by the methodology described in the document FINAT Test Method No. 1 (FINAT Technical Handbook, 6th edition, 2001). Thus, an article that adheres to the skin having defined dimensions and comprising a support on which the silicone adhesive is coated is applied by bringing the silicone adhesive into contact on a sheet of Bristol paper. The article is subsequently detached and the force is measured and related to the width of the article and is expressed in g/cm (or N/cm).

Silicone-based adhesives exhibit advantageous properties for biomedical applications. Unfortunately, as mentioned above, they are sensitive to sterilization by gamma rays and lose the tack properties suitable for an atraumatic use on the skin of patients.

The authors of the present invention have solved this problem and found, surprisingly, that it is now possible to develop a skin-adhesive article comprising a silicone adhesive which, after sterilization by gamma ($\gamma$) rays, maintains its tack properties suitable for use on the skin.

Thus, it is an object of the present invention to provide novel skin-adhesive articles which respond to the problems listed above.

This objective is achieved by the invention, which relates to a skin-adhesive article comprising a substrate F coated, continuously or noncontinuously, on at least one of the two faces with a pressure-sensitive silicone adhesive Z obtained by crosslinking a silicone composition X comprising:

1) from 80 to 20 parts by weight of at least one silicone resin A comprising SiOH functional groups,
2) from 20 to 80 parts by weight of at least one polyorganosiloxane G2 comprising at least two Si-vinyl functional groups at the chain end and which is a silicone gum having a consistency at 25° C. of between 200 mm/10 and 2000 mm/10,
3) a silicone base B1 capable of reacting by addition reactions, comprising:
    at least one organohydrosiloxane having at least two SiH functional groups in an amount sufficient to provide an SiH/Si-vinyl molar ratio of between 0.5:1 and 20:1,
    a catalyst of the addition reaction C2, and
    optionally an inhibitor of the addition reaction, and
4) at least one solvent S,
    with the condition according to which:
a) the amount of solvent S is determined so that the silicone composition X contains, by weight as solid content of silicone, from 20% to 80% and preferably from 40% to 70%, and
b) said skin-adhesive article is sterilized by means of gamma radiation at doses of between 10 kGy and 50 kGy.

The applicant company has employed significant research means and carried out numerous experiments in order to achieve this objective, inter alia, and, on completion of this, it has had the credit of finding, entirely surprisingly and unexpectedly, that an article coated with a pressure-sensitive silicone adhesive Z which has a specific composition and which crosslinks by polyaddition reactions makes it possible to obtain a product, after gamma irradiation, having a variation in the tack properties on the skin of less than 5% (measurements of the peel strengths). This is all the more surprising as it is very common that silicone adhesives are particularly known to undergo a significant detrimental change in their physical properties during a treatment by gamma radiation (phenomenon of excessive crosslinking, splitting of the macromolecules, cyclization, oxidation, and the like). This type of treatment is well known to result in a more intensive crosslinking and a radical splitting of the chains of the polymers, resulting in losses of physical properties of the silicone material (loss of flexibility, of tensile strength or resistance to elongation and/or an increase in the hardness).

The silicone resin A comprising SiOH functional groups can be chosen from conventional silicone resins, among which may be mentioned organosilicon resins prepared by cohydrolysis and cocondensation of chlorosilanes chosen from the group consisting of those of formulae $(R^5)_3SiCl$, $(R^5)_2Si(Cl)_2$, $R^5Si(Cl)_3$ and $Si(Cl)_4$. These resins are branched organopolysiloxane oligomers or polymers which are well known and which are commercially available. They exhibit, in their structure, at least two different siloxyl units chosen from those of formulae $(R^5)_3SiO_{1/2}$ (M unit), $(R^5)_2SiO_{2/2}$ (D unit), $R^5SiO_{3/2}$ (T unit) and $SiO_{4/2}$ (Q unit), at least one of these units being a T or Q unit. The $R^5$ radicals are distributed so that the resins comprise from approximately 0.8 to 1.8 $R^5$ radicals per silicon atom. Furthermore, these resins are not completely condensed and contain OH groups. The $R^5$ radicals are identical or different and are chosen from linear or branched $C_1$-$C_6$ alkyl radicals, $C_2$-$C_4$ alkenyl radicals, phenyl or 3,3,3-trifluoropropyl. Mention may be made, for example, as alkyl $R^5$ radicals, of the methyl, ethyl, isopropyl, tert-butyl and n-hexyl radicals and, as alkenyl radicals, of the vinyl or allyl groups. Preferably, the $R^5$ radicals are methyl, vinyl or hydroxyl groups. Mention may be made, as examples of silicone resin A, of MQ resins, MDQ resins, DT resins and MDT resins, it being possible for the OH groups to be carried by the M, D and/or T units, the content by weight of OH groups generally being between 0.2% and 10% by weight.

According to a specific embodiment, the silicone resin A comprising SiOH functional groups is chosen from the group consisting of:
a) hydroxylated silicone resins of $MQ^{(OH)}$ type which are copolymers comprising M and $Q^{(OH)}$ siloxy units of following formulae:

$$M=R^1R^2R^3SiO_{1/2}, \text{ and}$$

$$Q^{(OH)}=(OH)SiO_{3/2},$$

with optionally the presence of siloxy unit $Q=SiO_{4/2}$
b) hydroxlyated silicone resins of $MD^{Vi}Q^{(OH)}$ type which are copolymers comprising M, $D^{Vi}$ and $Q^{(OH)}$ siloxy units of following formulae:

$$M=R^1R^2R^3SiO_{1/2},$$

$$D^{Vi}=(Vi)(R^1)SiO_{2/2}, \text{ and}$$

$$Q^{(OH)}=(OH)SiO_{3/2},$$

with optionally the presence of siloxy unit $Q=SiO_{4/2}$
c) hydroxylated silicone resins of $MM^{Vi}Q^{(OH)}$ type which are copolymers comprising M, $M^{Vi}$ and $Q^{(OH)}$ siloxy units of following formulae:

$$M=R^1R^2R^3SiO_{1/2},$$

$$M^{Vi}=(Vi)(R^1)(R^2)SiO_{1/2}, \text{ and}$$

$$Q^{(OH)}=(OH)SiO_{3/2},$$

with optionally the presence of siloxy unit $Q=SiO_{4/2}$
d) hydroxlyated silicone resins of $MDT^{(OH)}$ type which are copolymers comprising M, D and $T^{(OH)}$ siloxy units of following formulae:

$$M=R^1R^2R^3SiO_{1/2},$$

$$D=R^1R^2SiO_{2/2},$$

$$T^{(OH)}=(OH)R^1SiO_{2/2}, \text{ and}$$

e) hydroxlyated silicone resins of $DT^{(OH)}$ type which are copolymers comprising D and $T^{(OH)}$ siloxy units of following formulae:

$$D=R^1R^2SiO_{2/2},$$

$$T^{(OH)}=(OH)R^1SiO_{2/2},$$

in which formulae the symbol Vi=a vinyl group and the symbols $R^1$, $R^2$ and $R^3$ are chosen, independently of one another, from:
- the linear or branched alkyl groups having from 1 to 8 carbon atoms and optionally substituted by one or more halogen atoms, and preferably chosen from the group consisting of the methyl, ethyl, isopropyl, tert-butyl and n-hexyl groups, and
- aryl or alkylaryl groups having from κ to 14 carbon atoms inclusive, and preferably chosen from the group consisting of the phenyl, xylyl and tolyl groups.

According to a preferred embodiment, the silicone resin A is a hydroxylated silicone resin of $MQ^{(OH)}$ or $MM^{Vi}Q^{(OH)}$ type and contains from 0.1% to 4% by weight of hydroxyl group with respect to the dry weight of said silicone resin A.

Use is made, in order to describe the polyorganosiloxanes, of the nomenclature known in the field of silicones and which uses, in order to describe siloxy units, the following letters: M, D, T and Q. The letter M represents the monofunctional unit of formula $(R)_3SiO_{1/2}$, the silicon atom being connected to just one oxygen atom in the polymer comprising this unit. The letter D means a difunctional unit $(R)_2SiO_{2/2}$ in which the silicon atom is connected to two oxygen atoms. The letter T represents a trifunctional unit of formula $(R)SiO_{3/2}$, in which the silicon atom is connected to three oxygen atoms. The letter Q represents a trifunctional unit of formula $SiO_{4/2}$ in which the silicon atom is connected to four oxygen atoms. The symbol R has the same definition as the symbols $R^2$, $R^3$ and $R^4$ defined below. The M, D and T units can be functionalized. Reference is then made to M, D and T units, while specifying the specific radicals.

The polyorganosiloxane G2 according to the invention preferably comprises the siloxy units of following formulae:

$$M^{Vi}=[(Vi)(R^2)_2SiO_{1/2}] \text{ and } D=[R^3R^4SiO_{2/2}]$$

in which formulae:
Vi=vinyl group; $R^2$, $R^3$ and $R^4$ are identical or different radicals chosen from the group consisting of:
- linear or branched $C_1$-$C_6$ alkyl radicals, such as, for example, methyl, ethyl, propyl, isopropyl, butyl, isobutyl, t-butyl, n-pentyl or n-hexyl,
- $C_3$-$C_8$ cycloalkyl radicals, such as, for example, cyclopentyl or cyclohexyl,
- $C_6$-$C_{10}$ aryl radicals, such as, for example, phenyl or naphthyl, and
- $C_7$-$C_{15}$ alkylaryl radicals, such as, for example, tolyl or xylyl.

More preferably still, the polyorganosiloxane G2 is an α,ω-bis(vinyl)polydimethylsiloxane, which means that the $R^2$, $R^3$ and $R^4$ radicals of the siloxy units of the polyorganosiloxane G2 are methyl radicals. The polyorganosiloxane G2 exhibits a dynamic viscosity of between 20 000 and 600 000 mPa·s at 25° C., preferably between 100 000 and 600 000 mPa·s at 25° C., or a consistency of between 200 and 2000, expressed as tenths of a millimeter at 25° C. (of between 200 mm/10 and 2000 mm/10). An α,ω-bis (vinyl)polydimethylsiloxane oil with a dynamic viscosity of between 20 000 and 600 000 mPa·s at 25° C. and an α,ω-bis(vinyl)polydimethylsiloxane gum with a consistency of between 200 and 2000, expressed as tenths of a millimeter at 25° C., are preferentially used as polyorganosiloxane G2.

The dynamic viscosity of the silicones is measured at 25° C. according to the standard ASTM D 445. The term "gum" is used for organosilicon compounds exhibiting viscosities conventionally of greater than or ~600 000 mPa·s, which corresponds to a molecular weight of greater than 260 000 g/mol. The consistency or penetrability of a gum is determined at 25° C. by means of a penetrometer of PNR12 type or equivalent model which makes it possible to apply, to the sample, a cylindrical head under standardized conditions. The penetrability of a gum is the depth, expressed in tenths of a millimeter, to which a calibrated cylinder penetrates into the sample over one minute. To this end, a sample of gum is introduced into an aluminum receptacle with a diameter of 40 mm and with a height of 60 mm. The cylindrical head, made of bronze or of brass, measures 6.35 mm in diameter and 4.76 mm in height and is carried by a metal rod with a length of 51 mm and with a diameter of 3 mm which fits the penetrometer. This rod is ballasted with an excess load of 100 g. The total weight of the assembly is 151.8 g, including 4.3 for the cylindrical part and its support rod. The receptacle containing the sample of gum is placed in the bath thermostatically controlled at 25±0.5° C., for at least 30 min. The measurement is carried out by following the instructions of the manufacturer. The values of the depth (V), in tenths of a millimeter, and of the time (t), in seconds, to reach this depth are shown on the device. The penetrability is equal to 60 V/t, expressed in tenths of a millimeter per minute.

According to one embodiment of the invention, the solvent S is chosen from the group consisting of: aliphatic $C_6$ to $C_{16}$ hydrocarbons, polydimethylsiloxanes comprising a trimethylsilyl end group having a viscosity of 0.65 to 5 mPa·s at 25° C., cyclic polydimethylsiloxanes, (3-octyl) heptamethyltrisiloxane, toluene, xylene, a $C_1$ to $C_8$ alkyl ester, a $C_2$ to $C_4$ carboxylic acid and their mixtures.

Mention may be made, as preferred $C_1$ to $C_8$ alkyl ester, of ethyl acetate.

The crosslinking to obtain the pressure-sensitive silicone adhesive Z is initiated by evaporating the solvent S, preferably while keeping the skin-adhesive article in a chamber within which the temperature is between 50° C. and 200° C., and preferably the temperature within the chamber is kept at plus or minus 5° C. from the boiling point of said solvent S.

The substrate can be a support of highly varied nature, according to the field of application. Mention may be made, for example of supports having a high surface energy, such as metals, aluminum or glass. Mention may also be made, for example, of plastics, such as films made of polyester, of polyimide, of polyethylene terephthalate, or certain polydimethylsiloxanes.

According to a preferred embodiment, the substrate F is a woven, nonwoven or knitted textile or a film of plastic. The term "nonwoven" is understood to mean any structure consisting of textile materials, such as fibers, continuous filaments or cut yarns, whatever the nature or the origin thereof, formed into a net by any means and bonded by any means, excluding the intertwining of yarns. Nonwovens are products having the appearance of textiles, are porous, are composed mainly of fibers and are manufactured by processes other than spinning, weaving, knitting or knotting.

According to another preferred embodiment, the substrate F is made of plastic. A large variety of plastics can be appropriate for use as substrate according to the invention. Examples comprise: polyvinyl chloride, polypropylene, regenerated cellulose, polyethylene terephthalate (PET) and polyurethane, in particular melt-blown polyurethane. The substrate F can be a perforated flexible polyurethane film or a continuous flexible polyurethane film. This flexible polyurethane film can be manufactured from melt-blown polyurethane. When the substrate F is a flexible polyurethane film, the thickness will generally be between 5 and 600 μm, preferably between 5 and 250 μm and more preferably still between 10 and 100 μm.

According to another preferred embodiment, the substrate F is a continuous flexible film which is permeable to air and impermeable to fluids. The film can exhibit a variable moisture vapor transmission rate (MVTR) according to the application targeted. A technique for measuring the moisture vapor transmission rate in liquid contact is described in the standard NF-EN 13726-2. Preferably, the flexible polyurethane film will be chosen so as to obtain a dressing having a moisture vapor transmission rate of greater than 300 g/m²/24 hours, preferably of greater than or equal to 600 g/m²/24 hours, preferably again of greater than or equal to 1000 g/m²/24 hours. According to another advantageous alternative form of the invention, the continuous flexible polyurethane film is perforated so as to be able to promote the circulation of the exudates.

Examples of organohydrosiloxane having at least two SiH functional groups are crosslinking agents or extenders comprising:
at least two siloxy units of formula (XL-1) and preferably at least three siloxy units of formula (XL-1):

(XL-1)

in which the symbol H represents a hydrogen atom, the symbol L represents an alkyl having from 1 to 8 carbon atoms inclusive or a $C_6$ to $C_{10}$ aryl, and the symbol e is equal to 0, 1 or 2; and
optionally other siloxy units of formula (XL-2):

(XL-2)

in which the symbol L represents an alkyl having from 1 to 8 carbon atoms inclusive or a $C_6$ to $C_{10}$ aryl, and the symbol g is equal to 0, 1, 2 or 3.

Mention may be made, as useful examples of organohydrosiloxane having at least two SiH functional groups which has a crosslinking function, of those of formulae $M^H D_x D_w{}^H M^H$, $M^H D_x D_y{}^H M$ and $MD_x D_z{}^H M$, in which formulae:
$M^H$=siloxyl unit of formula: (H) $(CH_3)_2 SiO_{1/2}$
$D^H$=siloxyl unit of formula: (H) $(CH_3) SiO_{2/2}$
D=siloxyl unit of formula: $(CH_3)_2 SiO_{2/2}$; and
M=siloxyl unit of formula: $(CH_3)_3 SiO_{1/2}$
with:
x is a number of between 0 and 500, preferably between 2 and 250 and more preferentially still between 5 and 80,
w is a number of between 0 and 500, preferably of between 1 and 250 or between 1 and 100 and more preferentially still of between 1 and 70;
y is a number of between 1 and 500, preferably of between 3 and 250 or between 2 and 100 and more preferentially still of between 2 and 70, and
z is a number of between 2 and 500, preferably of between 3 and 250 or between 3 and 100 and more preferentially still of between 3 and 70, and
comprising between 2.5% and 15.0% by weight of Si—H functional group per polymer, preferably between 3.0% and 15.0% by weight of Si—H functional group per polymer and more preferentially still between 3.5% and 12.5% by weight of Si—H functional group per polymer.

Mention may be made, as example of catalyst of the addition reaction C2 of use according to the invention, of the compounds of a metal belonging to the platinum group well known to a person skilled in the art. The metals of the platinum group are those known under the name of platinum-group metals, a term which brings together, besides platinum, ruthenium, rhodium, palladium, osmium and iridium. Preferably, platinum and rhodium compounds are used. Use may in particular be made of the complexes of platinum and of an organic product described in the patents U.S. Pat. Nos. 3,159,601, 3,159,602, 3,220,972 and the European patents EP-A-0 057 459, EP-A-0 188 978 and EP-A-0 190 530, of the complexes of platinum and of vinylated organosiloxanes described in the U.S. Pat. No. 3,419,593. The catalyst generally preferred is platinum. Mention may be made, by way of examples, of platinum black, chloroplatinic acid, a chloroplatinic acid modified by an alcohol, a complex of chloroplatinic acid with an olefin, an aldehyde, a vinylsiloxane or an acetylenic alcohol, inter alia. Preference goes to the Karstedt solution or complex, as described in the patent U.S. Pat. No. 3,775,452, to chloroplatinic acid hexahydrate or to a platinum catalyst comprising carbene ligands.

Mention may be made, as example of inhibitor of the addition reaction of use according to the invention, of that chosen from α-acetylenic alcohols, α,α'-acetylenic diesters, ene-yne conjugated compounds, α-acetylenic ketones, acrylonitriles, maleates, fumarates and the mixtures of these. These compounds, capable of performing the role of hydrosilylation inhibitor, are well known to a person skilled in the art. They can be used alone or as mixtures.

An inhibitor of α-acetylenic alcohol type can be chosen from the compounds of following formula (D1):

(D1)

in which:
the $R^1$ group represents an alkyl group, a cycloalkyl group, a (cycloalkyl)alkyl group, a $C_6$ to $C_{10}$ aryl group or a $C_7$ to $C_{18}$ arylalkyl group,
the $R^2$ group represents a hydrogen atom, an alkyl group, a cycloalkyl group, a (cycloalkyl)alkyl group, a $C_6$ to $C_{10}$ aryl group or a $C_7$ to $C_{18}$ arylalkyl group,
or else $R^1$ and $R^2$ constitute, together with carbon atom to which they are bonded, a 5-, 6-, 7- or 8-membered aliphatic ring optionally substituted one or more times.
According to the formula (D1):
the term "alkyl" is understood to mean a saturated hydrocarbon chain containing from 1 to 20 carbon atoms, preferably from 1 to 8 carbon atoms. An alkyl group can be chosen from the group consisting of methyl, ethyl, isopropyl, n-propyl, tert-butyl, isobutyl, n-butyl, n-pentyl, isoamyl and 1,1-dimethylpropyl;
the term "cycloalkyl" is understood to mean, according to the invention, a saturated monocyclic or polycyclic, preferably monocyclic or bicyclic, hydrocarbon group containing from 3 to 20 carbon atoms, preferably from 5 to 8 carbon atoms. When the cycloalkyl group is polycyclic, the multiple cyclic nuclei can be attached to one another via a covalent bond and/or via a spirane atom and/or be condensed to one another. A cycloalkyl group can be chosen from the group consisting of cyclopropyl, cyclobutyl, cyclopentyl, cyclohexyl, cycloheptyl, cyclooctyl, adamantane and norbornane;
the term "(cycloalkyl)alkyl" is understood to mean, according to the invention, a cycloalkyl group as defined above bonded to an alkyl group as also defined above;
the term "aryl" is understood to mean, according to the invention, an aromatic hydrocarbon group containing from 6 to 10 carbon atoms which is monocyclic or polycyclic. An aryl group can be chosen from the group consisting of phenyl, naphthyl and anthracenyl;
the term "arylalkyl" is understood to mean, according to the invention, an aryl group as defined above bonded to an alkyl group also as defined above.

According to a preferred embodiment, in the formula (D1), $R^1$ and $R^2$ constitute, together with a carbon atom to which they are bonded, an unsubstituted 5-, 6-, 7- or 8-membered aliphatic ring. According to another preferred embodiment, $R^1$ and $R^2$, which are identical or different, represent, independently of one another, a monovalent $C_1$ to $C_{12}$, preferably $C_1$ to $C_6$, alkyl group.

An inhibitor with an α-acetylenic alcohol of use according to the invention can be chosen from the group consisting of the following compounds: 1-ethynyl-1-cyclopentanol; 1-ethynyl-1-cyclohexanol (also known as ECH); 1-ethynyl-1-cycloheptanol; 1-ethynyl-1-cyclooctanol; 3-methyl-1-butyn-3-ol (also known as MBT); 3-methyl-1-pentyn-3-ol; 3-methyl-1-hexyn-3-ol; 3-methyl-1-heptyn-3-ol; 3-methyl-1-octyn-3-ol; 3-methyl-1-nonyn-3-ol; 3-methyl-1-decyn-3-ol; 3-methyl-1-dodecyn-3-ol; 3-methyl-1-pentadecyn-3-ol; 3-ethyl-1-pentyn-3-ol; 3-ethyl-1-hexyn-3-ol; 3-ethyl-1-heptyn-3-ol; 3,5-dimethyl-1-hexyn-3-ol; 3-isobutyl-5-methyl-1-hexyn-3-ol; 3,4,4-trimethyl-1-pentyn-3-ol; 3-ethyl-5-methyl-1-heptyn-3-ol; 3,6-diethyl-1-nonyn-3-ol; 3,7,11-trimethyl-1-dodecyn-3-ol (also known as TMDDO); 1,1-diphenyl-2-propyn-1-ol; 3-butyn-2-ol; 1-pentyn-3-ol; 1-hexyn-3-ol; 1-heptyn-3-ol; 5-methyl-1-hexyn-3-ol; 4-ethyl-1-octyn-3-ol and 9-ethynyl-9-fluorenol.

An inhibitor of α,α'-acetylenic diester type can be chosen from the compounds of following formula (D2):

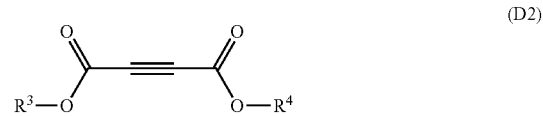

(D2)

in which the $R^3$ and $R^4$ groups, which are identical or different, represent, independently of each other, an alkyl group, a cycloalkyl group, a (cycloalkyl)alkyl group, a $C_6$ to $C_{10}$ aryl group, a $C_7$ to $C_{18}$ arylalkyl group or a silyl group.

The term "silyl" is understood to mean, according to the invention, a group of formula —$SiR_3$ in which each R symbol independently represents an alkyl group containing from 1 to 20 carbon atoms, preferably from 1 to 8 carbon atoms. A silyl group can be, for example, the trimethylsilyl group.

According to a specific embodiment, in the formula (D2), $R^3$ and $R^4$, which are identical or different, represent, independently of each other, a $C_1$ to $C_{12}$, preferably $C_1$ to $C_6$, alkyl group or the trimethylsilyl group. An inhibitor which is an α,α'-acetylenic diester of use according to the invention can be chosen from the group consisting of the following compounds: dimethyl acetylenedicarboxylate (DMAD), diethyl acetylenedicarboxylate, di(tert-butyl) acetylenedicarboxylate and bis(trimethylsilyl) acetylenedicarboxylate.

An inhibitor of ene-yne conjugated compound type can be chosen from the compounds of following formula (D3):

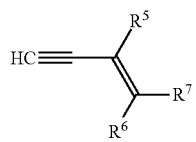

(D3)

in which:
the $R^5$, $R^6$ and $R^7$ groups represent, independently of one another, a hydrogen atom, an alkyl group, a cycloalkyl group, a (cycloalkyl)alkyl group, a $C_6$ to $C_{10}$ aryl group or a $C_7$ to $C_{18}$ arylalkyl group,
or also at least two groups from the $R^5$, $R^6$ and $R^7$ groups constitute, together with the carbon atom or atoms to which they are bonded, a 5-, 6-, 7- or 8-membered aliphatic ring optionally substituted one or more times.

According to a specific embodiment, the $R^5$, $R^6$ and $R^7$ groups represent, independently of one another, a hydrogen atom, a $C_1$ to $C_{12}$, preferably $C_1$ to $C_6$, alkyl group or a $C_6$ to $C_{10}$ aryl group. An inhibitor which is an ene-yne conjugated compound of use according to the invention can be chosen from the group consisting of the following compounds: 3-methyl-3-penten-1-yne; 3-methyl-3-hexen-1-yne; 2,5-dimethyl-3-hexen-1-yne; 3-ethyl-3-buten-1-yne; and 3-phenyl-3-buten-1-yne. According to another specific embodiment, two groups chosen from the $R^5$, $R^6$ and $R^7$ groups constitute, together with the carbon atom or atoms to which they are bonded, an unsubstituted 5-, 6-, 7- or 8-membered aliphatic ring and the remaining third group represents a hydrogen atom or a $C_1$ to $C_{12}$, preferably $C_1$ to $C_6$, alkyl group. An inhibitor which is an ene-yne conjugated compound of use according to the invention can be 1-ethynyl-1-cyclohexene.

An inhibitor of α-acetylenic ketone type can be chosen from the compounds of following formula (D4):

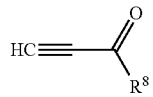

(D4)

in which: $R^8$ represents an alkyl group, a cycloalkyl group, a (cycloalkyl)alkyl group, a $C_6$ to $C_{10}$ aryl group or a $C_7$ to $C_{18}$ arylalkyl group, it being possible for the alkyl, cycloalkyl, (cycloalkyl)alkyl, aryl or arylalkyl groups to be optionally substituted one or more times by a chlorine, bromine or iodine atom.

According to a preferred embodiment, $R^8$ represents a monovalent $C_1$ to $C_{12}$, preferably $C_1$ to $C_6$, alkyl group optionally be substituted one or more times by a chlorine or bromine atom, or a cycloalkyl group, or a $C_6$ to $C_{10}$ aryl group. An inhibitor which is an α-acetylenic ketone of use according to the invention can be chosen from the group consisting of the following compounds: 1-octyn-3-one; 8-chloro-1-octyn-3-one; 8-bromo-1-octyn-3-one; 4,4-dimethyl-1-octyn-3-one; 7-chloro-1-heptyn-3-one; 1-hexyn-3-one; 1-pentyn-3-one; 4-methyl-1-pentyn-3-one; 4,4-dimethyl-1-pentyn-3-one; 1-cyclohexyl-1-propyn-3-one; benzoacetylene and (o-chlorobenzoyl) acetylene.

An inhibitor of acrylonitrile type can be chosen from the compounds of following formula (D5):

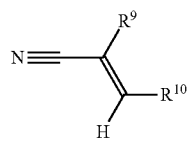

(D5)

in which: $R^9$ and $R^{10}$ represent, independently of each other, a hydrogen atom, a chlorine, bromine or iodine atom, an alkyl group, a cycloalkyl group, a (cycloalkyl)alkyl group, a $C_6$ to $C_{10}$ aryl group or a $C_7$ to $C_{18}$ arylalkyl group, it being possible for the alkyl, cycloalkyl, (cycloalkyl)alkyl, aryl or arylalkyl groups to be optionally substituted one or more times by a chlorine, bromine or iodine atom.

An inhibitor which is an acrylonitrile of use according to the invention can be chosen from the group consisting of the following compounds: acrylonitrile; methacrylonitrile; 2-chloroacrylonitrile; crotononitrile and cinnamonitrile.

An inhibitor of maleate or fumarate type can be chosen from the compounds of following formulae (D6) and (D7):

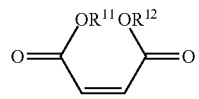

(D6)

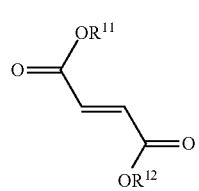

(D7)

in which: $R^{11}$ and $R^{12}$, which are identical or different, represent, independently of each other, an alkyl or alkenyl group, a cycloalkyl group, a (cycloalkyl)alkyl group, a $C_6$ to $C_{10}$ aryl group or a $C_7$ to $C_{18}$ arylalkyl group, it being possible for said alkyl, alkenyl, cycloalkyl, (cycloalkyl)alkyl, aryl and arylalkyl groups to be substituted by an alkoxy group.

The term "alkenyl" is understood to mean, according to the invention, a saturated hydrocarbon chain containing from 2 to 6 carbon atoms and comprising at least one double unsaturation. Preferably, the alkenyl group is chosen from the group consisting of a vinyl and an allyl. The term "alkoxy" is understood to mean, according to the formulae (D6) and (D7), an alkyl group as defined above bonded to an oxygen atom. An alkoxy group can be chosen from the group consisting of methoxy, ethoxy, propoxy and butoxy.

According to a specific embodiment, $R^{11}$ and $R^{12}$, which are identical or different, represent, independently of each other, a $C_1$ to $C_{12}$, preferably $C_1$ to $C_6$, alkyl or alkenyl group optionally substituted by a $C_1$ to $C_6$ alkoxy group.

An inhibitor which is a maleate or a fumarate of use according to the invention can be chosen from the group consisting of diethyl fumarate, diethyl maleate, diallyl fumarate, diallyl maleate and bis(methoxyisopropyl) maleate.

These inhibitors are added in an amount by weight of between 1 and 50 000 ppm, with respect to the weight of the total silicone composition, in particular between 10 and 10 000 ppm, preferably between 20 and 2000 ppm and more preferentially still between 20 ppm and 500 ppm.

According to one embodiment of the invention, the skin-adhesive article according to the invention is characterized in that it is a component of a dressing for medical or paramedical use.

According to another embodiment of the invention, the skin-adhesive article according to the invention is characterized in that it is a component of a wearable medical device.

Mention may be made, as technique for depositing the silicone composition X, for example, of the coating techniques carried out by a knife, in particular by knife overroll, floating knife and knife over carpet, or by padding, that is to say by squeezing between two rolls, or also by licking roll, rotary machine, reverse roll or transfer, or by spraying. Mention may be made, as other coating technique, of the curtain coating technique. Curtain coating is a process for application of a coating liquid to an article or a support. Curtain coating is characterized by the formation of a freely falling curtain of a coating liquid which falls from the lip of the hopper and, under the effect of gravity, will encounter the article moving through the curtain in order to form a coating. This technique has been widely used in the field of the preparation of multilayer photosensitive silver supports (see, for example, the U.S. Pat. Nos. 3,508,947, 3,508,947 and EP 537 086).

The silicone compositions according to the present invention possess highly advantageous properties and qualities. They can be crosslinked to give a pressure-sensitive adhesive, which justifies their use in the preparation of pressure-sensitive silicone adhesive compositions. For their part, the pressure-sensitive silicone adhesive compositions according to the invention in particular simultaneously possess noteworthy properties of tack and of peel strength.

This is because the main properties of PSA compositions are the tack and the peel strength. The tack characterizes the adhesiveness of a pressure-sensitive adhesive and brings two factors into play: the nature of the bonds which are instantaneously created with the support and the viscoelasticity of the adhesive. The peel strength makes it possible to evaluate the force necessary to separate an adhesive tape from its support.

These properties are illustrated below in the experimental part. They justify the use of the crosslinkable silicone compositions described above in the complete or partial coating of a surface of a support in order to confer adhesive properties on it, and also in a process for conferring adhesive properties on a support in which a surface of said support is completely or partially coated with a crosslinkable silicone composition described above, and then carries out the crosslinking, by evaporating the solvent, preferably by heating the silicone-treated support to a temperature which makes possible the departure of the solvent.

The examples which follow illustrate the present patent application.

Protocols of the Tests

1. Tack:

Standard ASTM D 2979 "Probe Tack". A metal rod connected to a force sensor is brought into contact with a sample with a rate of 1 cm/s. The contact time is one second. The force necessary to separate the rod from the film coated with the adhesive is measured and expressed in $g/cm^2$.

2. Peel Strength:

Standard ASTM D 330 A. The film coated with adhesive is applied to a metal sheet or a support of paper type (in order to simulate adhesion to the skin). After leaving for one minute, the film is detached from the sheet under an angle of 180° and at a constant rate of 300 mm/min. The peel strength is measured by a sensor in g/cm.

EXAMPLE 1: COMPARATIVE TESTS

Three commercial silicone gels supplied by Bluestar Silicones were prepared and coated continuously or non-continuously over a flexible polyurethane film and then subsequently sterilized by gamma radiation (at 16, and 50 kGy). The peel strength of the sterilized silicone gels was measured and compared with the peel strength without sterilization (the variations in % are mentioned in table 1).

Silicone gel 1: Silbione® HC2 2011
Silicone gel 2: Silbione® HC2 2022
Silicone gel 3: Silbione® HC2 2031

Measurement Conditions:

Peeling measurement on a sheet of Bristol paper (Exacompta, dimensions: 21 cm*5 cm)

Test specimen size: 2.5 cm×14 cm; peeling rate 300 mm/min—10 N cell—peeling over 12 cm.

TABLE 1

| | Variations in % of the peel strengths measured for the different silicone gels | | |
|---|---|---|---|
| | Peel strength variation after 16 kGy treatment | Peel strength variation after 30 kGy treatment | Peel strength variation after 50 kGy treatment |
| Gel 1 | −47% | −71% | −92% |
| Gel 2 | −48% | −78% | −88% |
| Gel 3 | −42% | −76% | −97% |

The peel strength (on a sheet of Bristol paper (simulating adhesion to the skin)) of the silicone gels decreases very strongly, even at low sterilization doses (16 kGy). The adhesion to the skin of devices using the gels 1, 2 and 3 after sterilization by gamma radiation is not satisfactory.

EXAMPLE 2: TESTS ACCORDING TO THE INVENTION

Three commercial pressure-sensitive silicone adhesives (PSAs) provided by Bluestar Silicones were prepared and coated continuously over a flexible polyethylene terephthalate (PET) film and then subsequently sterilized with gamma radiation (at 16 or 30 kGy). The peel strength of the sterilized silicone PSAs was measured and compared with the peel strength without sterilization (the variations in % are mentioned in table 2).

Silicone PSA 1: Silcolease® PSA 502 (PSA which crosslinks by platinum-catalyzed addition reactions).
Silicone PSA 2: Silcolease® PSA 400 (PSA which crosslinks by condensation reactions).
Silicone PSA 3: Silcolease® PSA 408 (PSA which crosslinks by condensation reactions).

Measurement Conditions:

Peeling measurement on a sheet made of stainless steel (provided by Cheminstrument, reference TP-26 Steel Panels)

Test specimen size: 2.5 cm×14 cm; peeling rate 300 mm/min—10 N cell—peeling over 12 cm.

TABLE 2

Variations in % of the peel strengths measured for the different silicone PSAs

| | Peel strength variation after 16 kGy treatment | Peel strength variation after 30 kGy treatment |
|---|---|---|
| Silicone PSA 1 (Invention) | −4% | −3% |
| Silicone PSA 2 (Comparative 1) | −14% | −17% |
| Silicone PSA 3 (Comparative 2) | −19% | −11% |

The best results are obtained with PSA 1, which is a pressure-sensitive adhesive which crosslinks by addition reactions (platinum catalyst). It is noticed that the peel strength of the silicone PSA 1 after irradiation is decreased by 3% to 4%, with respect to the same nonirradiated PSA, illustrating a change in the chemical structure of the product obtained after irradiation.

The silicone PSAs 2 and 3 (comparative), which are PSAs which crosslink by polycondensation, show variations in the peel strengths of between −10% and −15%, causing problems of adhesion, in particular when adhesion to the skin is concerned.

The invention claimed is:

1. A skin-adhesive article comprising a substrate F coated on at least one of the two faces with a pressure-sensitive silicone adhesive Z obtained by crosslinking a silicone composition X comprising:
   1) from 80 to 20 parts by weight of at least one silicone resin A comprising SiOH functional groups,
   2) from 20 to 80 parts by weight of at least one polyorganosiloxane G2 comprising at least two Si-vinyl functional groups at the chain end and which is a silicone gum having a consistency at 25° C. of between 200 mm/10 and 2000 mm/10,
   3) a silicone base B1 capable of reacting by addition reactions, comprising:
      at least one organohydrosiloxane having at least two SiH functional groups in an amount sufficient to provide an SiH/Si-vinyl molar ratio of between 0.5:1 and 20:1, and
      a catalyst of the addition reaction C2, and
   4) at least one solvent S,
   wherein:
   a) the amount of solvent S is determined so that the silicone composition X contains, by weight as solid content of silicone, from 20% to 80%,
   b) the crosslinking to obtain the pressure-sensitive silicone adhesive Z is initiated by evaporating the solvent S,
   c) said skin-adhesive article is sterilized by means of gamma radiation at doses of between 10 kGy and 50 kGy, and
   d) the article, after gamma irradiation, has a variation in the tack properties on skin of less than 5% as measured by peel strength.

2. The skin-adhesive article as claimed in claim 1, wherein the solvent S is selected from the group consisting of: aliphatic $C_6$ to $C_{16}$ hydrocarbons, polydimethylsiloxanes comprising a trimethylsilyl end group and having a viscosity of 0.65 to 5 mPas at 25° C., cyclic polydimethylsiloxanes, (3-octyl) heptamethyltrisiloxane, toluene, xylene, a $C_1$ to $C_8$ alkyl ester, a $C_2$ to $C_4$ carboxylic acid and their mixtures.

3. The skin-adhesive article as claimed in claim 1, wherein the silicone resin comprising SiOH functional groups is selected from the group consisting of:
   a) hydroxylated silicone resins of $MQ^{(OH)}$ type which are copolymers comprising M and siloxy units of following formulae:

$M = R^1R^2R^3SiO_{1/2}$, and $Q^{(OH)} = (OH)SiO_{3/2}$, b) hydroxylated silicone resins of $MD^{Vi}Q^{(OH)}$ type which are copolymers comprising M, $D^{Vi}$ and siloxy units of following formulae:

$M = R^1R^2R^3SiO_{1/2}$, $D^{Vi} = (Vi)(R^1)SiO_{2/2}$, and $Q^{(OH)} = (OH)SiO_{3/2}$, c) hydroxylated silicone resins of $MM^{Vi}Q^{(OH)}$ type which are copolymers comprising M, $M^{Vi}$ and siloxy units of following formulae:

$M = R^1R^2R^3SiO_{1/2}$, $D^{Vi} = (Vi)(R^1)SiO_{2/2}$, and $Q^{(OH)} = (OH)SiO_{3/2}$, d) hydroxylated silicone resins of $MDT^{(OH)}$ type which are copolymers comprising M, D and T(° H) siloxy units of following formulae:

$M = R^1R^2R^3SiO_{1/2}$, $D = R^1R^2SiO_{2/2}$, $T^{(OH)} = (OH)R^1SiO_{2/2}$, and e) hydroxylated silicone resins of $DT^{(OH)}$ type which are copolymers comprising D and $T^{(OH)}$ siloxy units of following formulae:

$D = R^1R^2SiO_{2/2}$, $T^{(OH)} = (OH)R^1SiO_{2/2}$, in which formulae the symbol Vi=a vinyl group and the symbols $R^1$, $R^2$ and $R^3$ are selected, independently of one another, from the group consisting of:
   linear or branched alkyl groups having from 1 to 8 carbon atoms and optionally substituted by one or more halogen atoms, and
   aryl or alkylaryl groups having from 6 to 14 carbon atoms inclusive.

4. The skin-adhesive article as claimed in claim 3, wherein the silicone resin A is a hydroxylated silicone resin of $MQ^{(OH)}$ or $MM^{Vi}Q^{(OH)}$ type and contains from 0.1% to 4% by weight of hydroxyl group with respect to the dry weight of said silicone resin A.

5. The skin-adhesive article as claimed in claim 1, wherein the article is a component of a dressing for medical or paramedical use.

6. The skin-adhesive article as claimed in claim 1, wherein the article is a component of a wearable medical device.

7. The skin-adhesive article as claimed in claim 1, wherein the amount of solvent S is determined so that the silicone composition X contains from 40% to 70% by weight as solid content of silicone.

8. The skin-adhesive article as claimed in claim 2, wherein the solvent S is evaporated while keeping the skin-adhesive article in a chamber within which the temperature is between 50° C. and 200° C.

9. The skin-adhesive article as claimed in claim 8, wherein the temperature within the chamber is kept at plus or minus 5° C. from the boiling point of said solvent S.

10. The skin-adhesive article as claimed in claim 3, wherein when $R^1$, $R^2$ and $R^3$ are, independently of one another, the linear or branched alkyl groups, $R^1$, $R^2$ and $R^3$ are selected from the group consisting of methyl, ethyl, isopropyl, tert-butyl and n-hexyl groups.

11. The skin-adhesive article as claimed in claim 3, wherein when $R^1$, $R^2$ and $R^3$ are, independently of one another, the aryl or alkylaryl groups, $R^1$, $R^2$ and $R^3$ are selected from the group consisting of the phenyl, xylyl and tolyl groups.

12. The skin-adhesive article as claimed in claim 1, wherein the hydroxlyated silicone resins of $MQ^{(OH)}$ type, the hydroxlyated silicone resins of $MD^{Vi}Q^{(OH)}$ type or the hydroxlyated silicone resins of $MM^{Vi}Q^{(OH)}$ type further comprise siloxy units $Q=SiO_{4/2}$.

13. The skin-adhesive article as claimed in claim 1, wherein the organohydrosiloxane having at least two SiH functional groups has the formula $M^H D_x D_w^H M^H$, $M^H D_x D_y^H M$ or $MD_x D_z^H M$, wherein:

$M^H$=siloxyl unit of formula: $(H)(CH_3)_2SiO_{1/2}$
$D^H$=siloxyl unit of formula: $(H)(CH_3)SiO_{2/2}$
$D$=siloxyl unit of formula: $(CH_3)_2SiO_{2/2}$; and
$M$=siloxyl unit of formula: $(CH_3)_3SiO_{1/2}$ where:
x is a number selected from the group consisting of between 0 and 500, between 2 and 250 and between 5 and 80,
w is a number selected from the group consisting of between 0 and 500, between 1 and 250, between 1 and 100 and between 1 and 70;
y is a number selected from the group consisting of between 1 and 500, between 3 and 250, between 2 and 100 and between 2 and 70, and
z is a number selected from the group consisting of between 2 and 500, between 3 and 250, between 3 and 100 and between 3 and 70.

14. The skin-adhesive article as claimed in claim 13, wherein the organohydrosiloxane having at least two SiH functional groups comprises between 2.5% and 15.0%, between 3.0% and 15.0% or between 3.5% and 12.5% by weight of SiH functional group per polymer.

15. The skin-adhesive article as claimed in claim 1, wherein the silicone base B1, further comprises an inhibitor of the addition reaction.

* * * * *